United States Patent [19]
Kassebaum et al.

[11] Patent Number: 5,258,359
[45] Date of Patent: Nov. 2, 1993

[54] GLYPHOSANT-CONTAINING HERBICIDAL COMPOSITIONS COMPRISING ACETYLENIC DIOL RAINFASTNESS ENHANCING AGENTS

[75] Inventors: James W. Kassebaum, Manchester; Miguel M. Dayawon, St. Louis; Joseph J. Sandbrink, Des Peres, all of Mo.

[73] Assignee: Monsanto Company, St. Louis, Mo.

[21] Appl. No.: 22,811

[22] Filed: Feb. 22, 1993

Related U.S. Application Data

[63] Continuation of Ser. No. 739,589, Aug. 2, 1991, abandoned.

[51] Int. Cl.$^5$ ............... A01N 25/24; A01N 57/04
[52] U.S. Cl. ....................... 504/206; 71/DIG. 1
[58] Field of Search ................ 504/206; 71/DIG. 1

[56] References Cited

U.S. PATENT DOCUMENTS

| | | | |
|---|---|---|---|
| 3,799,758 | 3/1974 | Franz | 71/86 |
| 4,011,062 | 3/1977 | Demchak et al. | 71/93 |
| 4,081,468 | 3/1978 | Baker et al. | 260/551 |
| 4,162,154 | 7/1979 | Gates et al. | 71/86 |
| 4,372,777 | 2/1983 | LeClair et al. | 71/DIG. 1 |
| 4,405,531 | 9/1988 | Franz | 260/501.12 |
| 4,628,092 | 12/1986 | Takahashi et al. | 544/351 |
| 4,783,342 | 11/1988 | Polovina | 427/4 |
| 4,806,275 | 9/1989 | Johnson et al. | 252/554 |

FOREIGN PATENT DOCUMENTS

| | | |
|---|---|---|
| 0220902 | 5/1987 | European Pat. Off. . |
| 0364202 | 4/1990 | European Pat. Off. . |

OTHER PUBLICATIONS

Tedeschi, "Surfynol ® Adjuvants-Greenhouse and Field Studies" (date unknown).
Air Products and Chemicals, Inc., "Surfynol ® TC-E" 1978, 1982.
Air Products and Chemicals, Inc., "Surfynol ® 400 Series Surfactants" (date unknown).
Air Products and Chemicals, Inc., "Surfynol ® Surfactants Performance in Agricultural Chemicals", 1980.

*Primary Examiner*—Richard L. Raymond
*Assistant Examiner*—S. Mark Clardy
*Attorney, Agent, or Firm*—Stanley M. Tarter; Gordon F. Sieckmann; Richard H. Shear

[57] ABSTRACT

New and useful herbicidal compositions comprising glyphosate and/or agriculturally acceptable salts and an acetylenic diol surfactant structurally characterized by a symmetrically substituted triple bond and adjacent hydroxyl groups or adjacent polymeric oxyalkylated units, and optionally a second surfactant, are provided.

12 Claims, No Drawings

GLYPHOSANT-CONTAINING HERBICIDAL COMPOSITIONS COMPRISING ACETYLENIC DIOL RAINFASTNESS ENHANCING AGENTS

This is a continuation of application Ser. No. 07/739,589 filed on Aug. 2, 1991, now abandoned.

FIELD OF THE INVENTION

The present invention relates to new and useful herbicidal compositions of N-phosphonomethylglycine or agriculturally acceptable salts thereof having enhanced herbicidal effectiveness and rainfastness and to a method of using such compositions to control vegetation.

BACKGROUND OF THE INVENTION

N-phosphonomethylglycine, also known by its common name glyphosate, and herbicidal salts thereof are highly effective and commercially important herbicides useful for combating the presence of a wide variety of unwanted vegetation. The herbicide is normally applied systemically or to the foliage of a very broad spectrum of annual and perennial grasses, broadleaf plants and the like. Once within the plant, the herbicide translocates and is lethal to the whole plant when used in an effective amount.

Usually, glyphosate is formulated in herbicidal compositions in the form of a water soluble salt. Commercially, glyphosate in the form of its monoisopropylamine salt is most often sold in concentrated aqueous solution which normally also contains an appreciable amount of a surfactant. The presence of a surfactant which may be ionic or nonionic provides more efficient utilization of glyphosate or its salts dissolved in aqueous solution as compared to like glyphosate-containing solutions to which no surfactant has been added. The more efficient utilization of glyphosate and/or its salts occurs independently of whether the surfactant is anionic, cationic, or nonionic.

When glyphosate-containing herbicides are applied to foliage, as opposed to being directly injected into the plants to be eradicated or controlled, the effectiveness thereof can be severely reduced if rain falls or if water is otherwise applied to the treated plants within a few hours after such application. The severity of the reduced efficacy of the herbicide is directly related to the amount and force of rainfall or applied water and is inversely related to the time that passes between application of the herbicide and the occurrence of rain or other application of water. The commercial label for the herbicide notes that rainfall or irrigation occurring within six hours after application to plants may reduce the effectiveness of the herbicide and that heavy rainfall or irrigation within two hours after application may wash the applied herbicide off the foliage, thereby possibly requiring retreatment of the plants.

Although various ingredients have been suggested for incorporation into aqueous glyphosate-containing solutions either to facilitate penetration of the herbicide into the plant or to hinder, prevent or otherwise restrict the removal of the herbicide from plant foliage by rainfall or other applications of water before the herbicide has entered the plant's systems in a sufficient amount to be lethal to the treated plants, the need for more effective rainfastening additives for glyphosate-containing aqueous solutions continues to exist. As used herein, the term "rainfastness" means the degree of effectiveness of the applied herbicidal composition to be retained notwithstanding a gentle spray of water, especially by rainfall. Improved resistance of glyphosate to being removed from the treated plants or otherwise being rendered less effective by water application is a long-felt need in the art.

Acetylenic diol surfactants have been suggested as an adjuvant for certain herbicides to increase the herbicidal activity via increased phytotoxicity against certain weeds. In a publication by Tedeschi entitled "Surfynol ® Adjuvant-Greenhouse and Field Studies," *Proc Northeast Weed Sci. Soc.*, 33 p 81-82 (1979) it is reported that certain Surfynol adjuvants show promise in increasing the herbicidal activities of atrazine, alachlor, bentazon and chloroxuron. There is no suggestion, as has now been discovered, that any such adjuvants would be useful in enhancing the rainfastness, as well as in enhancing the activity of a glyphosate-containing herbicide applied to plants from an aqueous solution.

It is often desirable to provide glyphosate and any potentiating surfactant in the form of a concentrated aqueous solution. However, it has been found that when acetylenic diol is used as the sole surfactant, a stable homogeneous concentrate formulation is not obtained, except at very low levels of the surfactant and/or at glyphosate salt concentrations around 15% or lower. As one increases the amount of acetylenic diol surfactant up to a point, a corresponding increase in the glyphosate activity will be gained. Unfortunately, when one adds acetylenic diol surfactants to an aqueous solution of glyphosate beyond a certain amount depending on the particular acetylenic diol used, temperature, concentration of glyphosate, etc., it has been found that the surfactant will phase separate, resulting in an unstable, nonhomogeneous formulation. In accordance with the present invention, it has been found that when acetylenic diol surfactants are used, together with at least one other surfactant of certain classes, acceptably stable, homogeneous concentrate glyphosate formulations can be obtained, in some cases also showing improved activity by comparison with formulations containing the acetylenic diol as the sole surfactant. The presence of the second surfactant raises the level of the diol which can be used in concentrates without occurrence of phase separation. Concentrates normally contain glyphosate in an amount requiring a dilution of at least 5 times and up to 100 times with water to have an optimum spray application rate. Suitable concentrates will contain about 5-40 weight percent of glyphosate acid equivalent. Among the second surfactants found useful for this purpose, for example, are included ethoxylated tertiary amines, ethoxylated quaternary amines, propoxylated quaternary amines, alkylglycosides, alkylpolyglycosides, nonalkoxylated amines, ethoxylated amine oxides, nonethoxylated amine oxides, and the like.

Rainfastness of glyphosate-containing aqueous solutions is of particular importance in Southeast Asia, Florida, and similar geographic locations where rainfall often occurs with great frequency and sometimes with considerable force. Often in these areas there is simply not enough time between rainfalls to provide for the highest and best use of glyphosate-containing herbicides. With short time intervals between heavy rainfalls, the herbicide can be washed away or otherwise rendered less useful before it has had time to translocate inside the treated plant so as to be fully effective as a herbicide.

It is known that an ethoxylated siloxane, sold as a tank mix adjuvant under the name Silwet L-77 (hereinafter referred to as "L-77" for brevity), provides a limited amount of rainfastness for glyphosate-containing herbicides. L-77 contains as its main active ingredient a member of the silicone-polyethylene copolymer chemical family. More specifically, the active ingredient is polyalkylene oxide modified heptamethyltrisiloxane. Even more specifically, the active ingredient is 1,1,1,3,5,5,5-heptamethyltrisiloxanyl propyl-omega methoxy-poly(ethylene oxide) where the average number of ethylene oxide units is seven or so.

But, the high cost of L-77, its tendency to form a separate layer in concentrates on standing, thereby requiring stirring to have a homogenous solution, its chemical instability in glyphosate-containing solutions, and its tendency to antagonize glyphosate activity in the absence of rain, limit the use of L-77 for such purpose.

In accordance with the present invention, it has also been found that certain acetylenic diol surfactants when used with a second surfactant provide appreciably improved rainfastness to foliar-applied aqueous solutions of glyphosate and/or its agriculturally acceptable salts. In addition, these diol surfactants often enhance the herbicidal activity of the glyphosatecontaining solutions even in the absence of rain. The compositions of the present invention can be formulated as concentrates or tank mixes. The combinations of surfactants are also useful as tank mix adjuvants for aqueous glyphosate-containing solutions.

SUMMARY OF THE INVENTION

The present invention provides an aqueous composition comprising water, a herbicidally effective amount of glyphosate and/or at least one agriculturally acceptable salt of glyphosate and a rainfastness or glyphosate activity enhancing amount of at least one acetylenic diol structurally characterized by a symmetrically substituted triple bond and adjacent hydroxyl groups or adjacent hydroxyl groups which have been oxyalkylated. The aqueous composition in concentrated form contains a second surfactant in an amount to prevent the acetylenic diol from phase separating. In another embodiment, a dry concentrate formulation is provided comprising a herbicidally effective amount of glyphosate and/or at least one of its salts and a rainfastness or glyphosate activity enhancing amount of at least one acetylenic diol structurally characterized as above. Suitable dry concentrates will contain from 10 to 90 weight percent of glyphosate equivalent. The aqueous or dry composition is useful in controlling vegetation either by application of a dilute solution thereof to the foliage or by injection thereof into a translocation system of the vegetation. The use of the acetylenic diol adjuvant surprisingly increases both the rainfastness and herbicidal efficacy of the glyphosatecontaining solutions. Moreover, the use of the second surfactant extends the ability of increasing the amounts of the diol in aqueous concentrates.

DETAILED DESCRIPTION OF THE INVENTION

Glyphosate is the common name for N-phosphonomethylglycine. In the principal commercial composition glyphosate is formulated as the isopropylamine salt. Glyphosate solubility in water at 25° C. is about 1.2% by weight. For convenience glyphosate is best formulated as a water soluble salt. Glyphosate-isopropylamine is virtually completely soluble in water. Glyphosate is a relatively nonselective, nonresidual post-emergent herbicide. It is particularly effective on deep rooted perennial species, annual and biennial species of grasses, sedges, and broadleaved weeds. Excellent control of most species can be obtained at rates of 0.112 kg (a.i.)/ha to 11.2 kg a.i./ha. The term "a.i." refers to the amount normally expressed in kilograms (kg) per hectare (ha) of the active ingredient. Since the activity of glyphosate salts is more or less independent of the cationic species, such as isopropylammonium, sodium, potassium, trimethylsulfonium, and the like, which does not contribute in any significant way to the activity, it may be preferred to refer to the amount of active glyphosate ingredient in terms of acid equivalency which is conventionally abbreviated as "a.e."

In this specification and the following claims, numerical values are not critical unless otherwise stated. That is, the numerical values may be read as if they were prefaced with the word "about" or "substantially".

Since glyphosate is best formulated as a water-based solution of the isopropylamine salt, it has the drawback of being easily washed off the treated vegetation to which it has been applied or rendered less effective before there has been enough time to pass for an effective amount of the herbicide to translocate from the foliar surface of the treated vegetation to inside the vegetation where the herbicidal effect occurs.

To enhance the rainfastness of the applied glyphosate and/or glyphosate salt in accordance with the present invention, a rainfastness-enhancing effective amount of at least one acetylenic diol is used as a rainfastness adjuvant in glyphosate-containing aqueous solutions. To obtain this desired result for each part of glyphosate, one can employ about 0.01 to about 1 part of the acetylenic diol. The ratio of glyphosate to diol may vary depending upon a variety of factors, such as the identity of the diol, the target weeds and whether the composition is intended to be an adjuvant or is a ready to use composition.

In the preparation of aqueous concentrates, a second surfactant is used in an amount sufficient to inhibit or suppress the diol from separating as a second phase. To obtain this desired result for each part of glyphosate, one can employ about 0.01 to about 1 part of the second surfactant. The ratio of glyphosate to the second surfactant may vary depending upon a variety of factors, such as the identity of the cosurfactant, the target weeds, etc. The acetylenic diol and any other surfactants are present in the composition in a weight ratio of 10:1 to 1:10 with respect to each other. Preferably, the rate is in the range of 5:1 to 1:5.

The second surfactant may be one or more substances selected from alkyl glycoside or alkyl polyglycoside surfactants, ethoxylated tertiary amine surfactants, ethoxylated quaternary amine surfactants, propoxylated quaternary amine surfactants, nonalkoxylated amine surfactants, nonethoxylated amine oxide surfactants, and ethoxylated amine oxide surfactants.

The alkyl glycoside and alkyl polyglycoside surfactants useful as second surfactants in accordance with the present invention can be depicted by the following molecular structure:

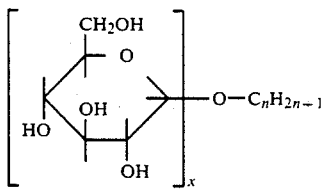

wherein n is an integer of about 8-18, preferably about 9-12 and x is 1 to about 8, preferably 1 to about 3 with an average value most preferably being about 1.2 to 1.8.

The ethoxylated quaternary amine surfactants useful as a second surfactant in accordance with the present invention can be depicted by the following molecular structure

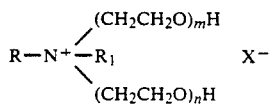

wherein R is a $C_{8-20}$ alkyl, preferably a $C_{12-18}$ alkyl, and m+n total 2 to about 25, preferably 10 to 15. Most preferably, when R is $C_{12}$, then m+n is 2 and when R is $C_{18}$, then m+n is 15. X is any suitable counterion, such as a halogen and preferably, chlorine.

The ethoxylated amine surfactants useful as a second surfactant in accordance with the present invention can be depicted by the following molecular structure

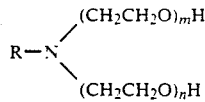

where R is a $C_{8-20}$ alkyl, preferably a $C_{12-18}$ alkyl, and m+n total 2 to about 25, preferably 10-15. Most preferably, when R is $C_{12}$, then m+n is 2 and when R is $C_{18}$, then m+n is 15.

The propoxylated quaternary amine surfactants useful as a second surfactant in accordance with the present invention can be depicted by the following structural formula $$R_3 N-[EO-(PO)_n]-H^+X^-$$

where each R is independently methyl, ethyl or hydroxy $C_1-C_3$ alkylene, EO is ethylene oxide, PO is propylene oxide, and n is about 6-10 and X is a suitable counterion as above defined.

In addition to the active ingredient and the diol surfactant and cosurfactant, any of a variety of addititments and other adjuvants may be included in the formulated material of the present invention as long as such added materials are not significantly antagonistic to the glyphosate herbicidal activity and/or to the diol rainfastness-enhancing and/or herbicidal-enhancing activity. In addition to glyphosate or its salts, mixtures thereof with other herbicides are also part of this invention. Herbicides compatible with glyphosate and its salts include, for example, bialaphos, glufosinate, 2,4-D, MCPA, dicamba, diphenylethers and sulfonylureas.

The rainfastness-enhancing and glyphosate activity-enhancing acetylenic diol added to the water-based formulations of glyphosate and/or its salts in accordance with the present invention is structurally characterized by a symmetrically substituted triple bond and adjacent hydroxyl groups which may or may not be oxyalkylated with ethylene oxide, propylene oxide or both ethylene oxide and propylene oxide.

The acetylenic diols which may be used in accordance with the present invention to enhance rainfastness and/or herbicidal effectiveness of water-based formulations of glyphosate and/or its salts correspond to the following structural formula

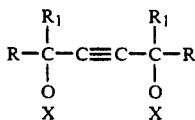

wherein each X is independently hydrogen or $(R_2O)_n$—H where $R_2$ is ethylene or propylene and n is the average number of repeating alkylene oxide units. Each n is a number of 1 to about 100, preferably 1 to 50. Thus, the total alkylene oxide units may range to a total of 200. The oxyalkylated adducts are readily prepared by condensing the dihydroxyl acetylenic compounds with ethylene oxide or propylene oxide in the presence of a basic catalyst in a well-known manner. Preferably, $R_2$ is ethylene. R is hydrogen or a lower alkyl group, either branched or straight chain containing 1 to about 6 carbon atoms, e.g., methyl, ethyl, propyl, isopropyl, n-butyl, isobutyl, pentyl, etc. $R_1$ is a radical selected from the group consisting of methyl, ethyl, cyclopropyl and phenyl.

Representative compounds providing suitable rainfastness enhancement include:
2,4,7,9-tetramethyl-5-decyne-4,7-diol,
4,7-dimethyl-5-decyne-4,7-diol,
2,3,6,7-tetramethyl-4-octyne-3,6-diol,
3,6-dimethyl-4-octyne-3,6-diol,
2,5-dicyclopropyl-3-hexyne-2,5-diol,
3,6-dimethyl-4-octyne-3,6-diol,
2,5-diphenyl-3-hexyne-2,5-diol,
2,5-dimethyl-3-hexyne-2,5-diol,
5,8-dimethyl-6-dodecyne-5,8-diol,
2,5,8,11-tetramethyl-6-dodecyne-5,8-diol,
and the like.

Representative ethoxylated acetylenic diols include the following wherein the amount of ethylene oxide reacted with the acetylenic diol is indicated as EO with the prefix number being the average total EO units per molecule:
2,4,7,9-tetramethyl-5-decyne-4,7-diol+3.5EO
4,7-dimethyl-5-decyne-4,7-diol+200EO
2,3,6,7-tetramethyl-4-octyne-3,6-diol+10EO
3,6-diethyl-4-octyne-3,6-diol+9EO
2,5-dicyclopropyl-3-hexyne-2,5-diol+20EO
3,6-dimethyl-4-octyne-3,6-diol+30EO
2,4,7,9-tetramethyl-5-decyne-4,7-diol+15EO
4,7-dimethyl-5-decyne-4,7-diol+20EO
2,3,6,7-tetramethyl-4-octyne-3,6-diol+2EO
3,6-diethyl-4-octyne-3,6-diol+100EO
2,5-dicyclopropyl-3-hexyne-2,5-diol+50EO
3,6-dimethyl-4-octyne-3,6-diol+20EO
2,5-diphenyl-3-hexyne-2,5-diol+30EO
2,5-dimethyl-3-hexyne-2,5-diol+10EO
5,8-dimethyl-6-dodecyne-5,8-diol+5EO
2,4,7,9-tetramethyl-5-decyne-4,7-diol+20EO
4,7-dimethyl-5-decyne-4,7-diol+8EO
2,3,6,7-tetramethyl-4-octyne-3,6-diol+12EO
3,6-diethyl-4-octyne-3,6-diol+15EO 2,5-dicyclopropyl-3-hexyne-2,5-diol + 10EO
3,6-dimethyl-4-octyne-3,6-diol + 50EO
2,4,7,9-tetramethyl-5-decyne-4,7-diol + 30EO
4,7-dimethyl-5-decyne-4,7-diol + 10EO
2,3,6,7-tetramethyl-4-octyne-3,6-diol + 5EO
3,6-diethyl-4-octyne-3,6-diol + 2EO
2,5-diphenyl-3-hexyne-2,5-diol + 5EO
2,5-dimethyl-3-hexyne-2,5-diol + 20EO
5,8-dimethyl-6-dodecyne-5,8-diol + 10EO
and the like.

It has been found that, with most things considered, 2,4,7,9-tetramethyl-5-decyne-4,7-diol, 2,5,8,11-tetramethyl-6-dodecyne-5,8-diol, and the oxyethylates thereof are the most preferred rainfastness enhancers of this invention.

The use of acetylenic diols, as opposed to the use of L-77 siloxane, results in significant improvements in that as a rule lower levels of the acetylenic diol to obtain the rainfastness quality of a prescribed amount of L-77 siloxane are needed. Also, it has been found that there is no appreciable antagonism of the glyphosate activity even in the absence of rain with the acetylenic diols. Detectable antagonism of the glyphosate activity results with the use of L-77 siloxane when a humectant is not employed. The need for using a humectant in the compositions of the present invention does not exist. Furthermore, L-77 siloxane in time will degrade in glyphosate-containing formulations, whereas the acetylenic diols used in the present invention have excellent stability and long shelf life when formulated in aqueous solution with glyphosate.

The herbicidal compositions of the invention may be applied in various ways, including topically as a spray to foliage as a postemergence herbicide and they may be sorbed in powder or granular or encapsulated. Compositions of the invention are typically water based and may include ingredients in addition to the glyphosate, diol and second surfactant, such as other active herbicides, stabilizers, solubility enhancing materials, etc. Also, the compositions may be in the form of a wettable powder, water soluble granules, tablets and briquettes.

The following examples merely illustrate the practice of the present invention. Obviously, the invention is not limited thereto. In the examples, all weights and percentages are given on a percent weight basis unless otherwise indicated.

In some of the examples, growth chambers were used to determine the comparative rainfastness and activity responses of selected plant species to various glyphosate herbicidal compositions containing and not containing various acetylenic diols as above defined. In each test carried out in a growth chamber, seeds or their seed equivalents of the selected plants were planted in 4-inch (10.2 cm) square pots containing straight soil and a fertilizer. In a growth chamber using cool growing conditions, the plants were grown at 18° C. day, 12° C. night, with a 10 hour photoperiod employing only fluorescent lights. The treatments were applied post-emergence to the plants after a selected growth period using a conventional fine spray device disposed overhead of the plants. The spray volumes of the tested herbicidal compositions were equivalent to 20 gallons per acre (187 l/ha) and were applied at a pressure of 30 pounds per square inch (207 kiloPascals). After spray application, the potted plants were replaced in the growth chamber with the same growth conditions being employed until completion of the tests. Percent control of the plants was noted after a predetermined time period.

In other examples, greenhouses were used to determine the comparative rainfastness and activity responses. The tests conducted in a greenhouse followed the same general procedure as in the growth chamber except that in the greenhouse the temperature was maintained at approximately 29° C. during the day and 21° C. during the night with a daily photoperiod of approximately 10–14 hours of daylight. Assessment of Percent Inhibition was made by comparison with untreated control pots on an arbitrary scale of 0 to 100% where 0 means no visible effect and 100 means death of all plants.

Examples of field tests are also given in which treatments are applied postemergence to indigenous plants or plants which had been mechanically seeded in rows. The photoperiod and temperatures depended on the actual climatic conditions extant at the time of treatments.

In the examples the aqueous solution composed of 2 parts of glyphosate (a.e.) and 1 part of ethoxylated (15 EO) tallowamine surfactant with the remainder being water is given the designation "RU." Specifically, RU is composed of 41% of the isopropylamine salt (a.i.) and 15% of the surfactant.

In the tank mixes various surfactants were mixed in tanks with RU. In the tables the added diol is given on a volume/volume (v/v) basis.

In the tests, 2,4,7,9-tetramethyl-5-decyne-4,7-diol + 1.3 EO is designated Diol 1. Diol 2 has the same diol adduct as Diol 1 but with 3.5 moles of ethylene oxide. Diol 3 has the same diol adduct as Diol 1 but with 10 moles of ethylene oxide. Diol 4 has the same diol adduct as Diol 1 but with 30 moles of ethylene oxide. Diol 5 has the same diol adduct as Diol 1 but with no ethylene oxide units. Diol 6 has the same diol adduct as Diol 1 but with 7.7 moles of ethylene oxide. Diol 7 has the same diol adduct as Diol 1 but with 20.5 moles of ethylene oxide. Diol 8 has the same diol adduct as Diol 1 but with 15.4 moles of ethylene oxide. Diol 9 has the same diol adduct as Diol 1 but with 20.5 moles of ethylene oxide.

In the following tables, the percent inhibitions of the tested plant species using various application rates of the glyphosate-containing compositions containing the ethoxylated tallowamine surfactant and glyphosate-containing compositions to which various amounts of the selected diols had been added have been set forth where no rain equivalent was applied and in many cases where a selected rain equivalent of 0.6 cm was applied one hour after treatment unless otherwise indicated. In the tables, the term "DAT" refers to the number of days transpiring after treatment before the % Inhibition was determined. The term "DAP" refers to the number of growing days transpiring between the planting date and the date of treatment. The term "GC" indicates that the test was carried out in a growth chamber. The term "GH" indicates that the test was carried out in a greenhouse. The term "FT" indicates that the test was carried out in the field. The term "IPA gly" refers to the monoisopropyl amine salt of glyphosate. In the various test results which follow, many of the treated plant species can be identified by reference to the following listing.

| Abbreviation | Plant Species | |
|---|---|---|
| DB | downy brome | *Bromus tectorum* |
| IM | indian mustard | *Brassica juncea* |

-continued

| Abbreviation | Plant Species | |
|---|---|---|
| RQG | rhizome quackgrass | *Elymus repens* |
| WT | wheat | *Triticum aestivum* |
| GG | guineagrass | *Panicum maximum* |
| RF | redstem filaree | *Erodium cicutarium* |
| BG | barnyardgrass | *Echinochloa crusgalli* |
| VL | velvetleaf | *Abutilon teophrasti* |
| RYE | annual ryegrass | *Lolium multiflorum* |
| MAL | Cheeseweed | *Malva sylvestris* |
| AB | annual bluegrass | *Poa annua* |
| TG | torpedograss | *Panicum repens* |

In the various tests several formulations were prepared and applied to the treated plants. These formulations (Formu) are identified as follows and percentages of components are given as a weight/weight basis.

| | Composition | |
|---|---|---|
| Formu A | 41% | IPA gly |
| | 12% | DOD (Dodigen 4022) |
| | 3% | Diol 3 |
| | 44% | water |
| Formu B | 24.8% | IPA gly |
| | 19.8% | Ethoquad C/12W (35% a.i.) |
| | 10.3% | L-77 |
| | 2.5% | propylene glycol |
| | 42.6% | water |
| Formu C | 24.8% | IPA gly |
| | 19.8% | Ethoquad C/2W (35% a.i.) |
| | 10.3% | Diol 3 |
| | 2.5% | propylene glycol |
| | 42.6% | water |
| Formu D | 41.2% | IPA gly |
| | 8.0% | Ethomeen T25 |
| | 2.0% | PEG (polyethylene glycol MW = 400) |
| | 3.0% | Diol 3 |
| | 45.8% | water |
| Formu E | 41.2% | IPA gly |
| | 11.0% | Ethoquad 18/25 |
| | 2.8% | PEG 400 |
| | 45.0% | water |
| Formu F | 41.2% | IPA gly |
| | 8.0% | Ethoquad 18/25 |
| | 2.0% | PEG 400 |
| | 3.0% | Diol 3 |
| | 45.8% | water |
| Formu G | 41.4% | IPA gly |
| | 15.0% | EMCOL CC-9 |
| | 43.6% | water |
| Formu H | 41.4% | IPA gly |
| | 10.0% | EMCOL CC-9 |
| | 5.0% | Diol 3 |
| | 43.6% | water |
| Formu I | 41.5% | IPA gly |
| | 21.4% | Ethoquad C/12W (35% a.i.) |
| | 37.1% | water |
| Formu J | 41.5% | IPA gly |
| | 10.0% | Ethoquad C/12W (35% a.i.) |
| | 4.0% | Diol 3 |
| | 44.5% | water |
| Formu K | 41.1% | IPA gly |
| | 15.4% | APG 32 (70% a.i.) |
| | 43.5% | water |
| Formu L | 41.0% | IPA gly |
| | 10.7% | APG 325 (70% a.i.) |
| | 3.5% | Diol 3 |
| | 44.8% | water |

EXAMPLE 1

In this example a comparison was made of the rainfastness obtained when Silwet L-77 surfactant was used with RU and when Diol 3 was used with RU as a tank mix in the greenhouse and growth chambers. The data of this example are set forth in the following three tables and represent averaged data of six tests, each of which had three replicates. In the examples the treated plant species are identified by the use of the plant abbreviations listed above. In the parentheses following each plant abbreviation, the first number provides the application rate of glyphosate in terms of kg a.e./ha, the second number is DAP as defined above or the height of the treated plant in centimeters (cm), and the third number is DAT, as defined above. The final two letters indicate whether the tests were conducted in a greenhouse growth chamber, or field. Thus, the following test descriptor "DB (0.43/23/28) in GC" is understood to mean that downy brome (DB) was treated in a growth chamber (GC) with glyphosate being applied at a rate of 0.43 kg a.e./ha. The treatment was made 23 days after planting; and the % Inhibitions were read and recorded 28 days after treatment.

In this example the tests were DB (0.43/23/28) in GC, IM (0.43/23/28) in GC (two tests), RQG (0.43/54/27) in GC, WT (0.14/23/27) in GC, and GG (0.43/25/25) in GH.

The average results of the six tests, each with three replicates, are set out in Table 1.

TABLE 1

| | % Inhibition | |
|---|---|---|
| Herb. Compoosition | 0 Rain | Rain |
| RU | 71 | 27 |
| RU + 0.125% Diol 3 | 90 | 56 |
| RU + 0.125% L-77 | 64 | 44 |

The results of an additional test with three replicates for GG (0.84/22/26) in GH are set out in Table 2.

TABLE 2

| | % Inhibition | |
|---|---|---|
| Herb. Composition | 0 Rain | Rain |
| RU | 77 | 27 |
| RU + 0.25% Diol 3 | 92 | 70 |
| RU + 0.25% L-77 | 79 | 43 |

The average results of three tests, each with three replicates, for IM (0.43/23/28) in GC, GG (0.17/25/25) in GH, and GG (0.84/22/26) in GH are set out in Table 3.

TABLE 3

| | % Inhibition | |
|---|---|---|
| Herb. Composition | 0 Rain | Rain |
| RU | 93 | 39 |
| RU + 0.5% Diol 3 | 97 | 79 |
| RU + 0.5% L-77 | 93 | 59 |

From this example it is seen that both the tested acetylenic diol and the tested siloxane provide some improved rainfastness for the plant species tested but that the acetylenic diol is more effective than L-77 at equal concentrations, both in the presence and absence of rainfall. Furthermore, the tested acetylenic diol enhanced glyphosate plant control in the absence of rain.

EXAMPLE 2

In the example a comparison was made of the rainfastness obtained when RU was used, when IPA glyphosate and Ethoquad C/12W surfactant were used in aqueous solution, and when Ethoquad C/12W surfactant plus Diol 3 were used in aqueous solution.

Ethoquad C/12W contains 35% (in water) of the methyl 2EO quaternary ammonium chloride having the following structural formula:

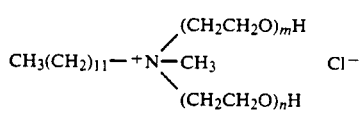

m+n=2 on average

The average results of one test with three replicates for GG (1.7/32/34) in GH are set out in Table 4. Ethoquad C/12W was used in amount to provide an application rate of 0.83 kg. active surfactant/ha.

TABLE 4

| Herb. Composition | % Inhibition | |
|---|---|---|
| | 0 Rain | Rain |
| RU | 100 | 40 |
| IPA gly + Ethoquad C/12W | 100 | 50 |
| IPA gly + Ethoquad C/12W + 0.25% Diol 3 | 100 | 90 |
| IPA gly + Ethoquad C/12W + 0.5% Diol 3 | 100 | 100 |

From the above data it can be seen that under the test conditions the rainfastness of glyphosate when used on GG with the cosurfactant mixture of Diol 3 and Ethoquad C/12W is much improved as compared with the use of the ethoxylated tallowamine surfactant alone in the RU composition or with Ethoquad C/12W alone.

EXAMPLE 3

In this example a comparison was made of the rainfastness obtained when RU was used at a rate of 1.4 kg a.e./ha active and when IPA glyphosate was used at the same acid equivalent rate with DOD surfactant plus Diol 3. DOD is a propoxylated quaternary trimethyl amine having the general formula $(CH_3)_3N[EO(PO)_8]$—$H^+Cl^-$ wherein EO means ethylene oxide and PO means propylene oxide.

The average results of one test of three replicates for RQG (1.4/42/20) in GC are set out in Table 5. Rain was applied three hours after treatment.

TABLE 5

| Herb. Composition | % Inhibition | |
|---|---|---|
| | 0 Rain | Rain |
| RU | 68 | 33 |
| Formu A | 88 | 83 |

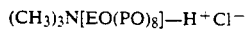

From the above data it can be seen that the rainfastness of glyphosate when formulated with the cosurfactant composition of DOD plus Diol 3 is much improved as compared to the use of the ethoxylated tallowamine surfactant alone which is present in RU.

EXAMPLE 4

In this example a comparison was made of the rainfastness when RU was used at a rate of 0.84 kg a.e./ha active, when IPA glyphosate was used at the same acid equivalent rate with Silwet L-77 and Ethoquad C/12W in aqueous solution, and when IPA glyphosate was used at the same active equivalent rate with Diol 3 and Ethoquad C/12W in aqueous solution.

The average results of two tests, each with three replicates, for GG (0.84/25/25) in GH and GG (0.84/46/27) in GH are set out in Table 6.

TABLE 6

| Herb. Composition | % Inhibition | |
|---|---|---|
| | 0 Rain | Rain |
| RU | 100 | 17 |
| Formu B | 82 | 12 |
| Formu C | 95 | 48 |

The average results of two additional tests, each with three replicates, for GG (1.7/25/25) in GH and GG (1.7/46/27) in GH are set out in Table 7.

TABLE 7

| Herb. Composition | % Inhibition | |
|---|---|---|
| | 0 Rain | Rain |
| RU | 100 | 34 |
| Formu B | 100 | 50 |
| Formu C | 100 | 69 |

From the above it is seen that Diol 3 when used with Ethoquad C/12w enhances the rainfastness of glyphosate to a significantly greater extent than L-77 with Ethoquad C/12W or the ethoxylated tallowamine in RU.

EXAMPLE 5

In this example a comparison was made of the rainfastness when RU was used at a rate of 1.7 kg a.e/ha active, when RU was used at the same rate with Silwet L-77, when IPA glyphosate was used at the same active rate with Silwet-77 and Ethoquad C/12W, and when RU was used at the same rate with Diol 3 at two different rate levels.

The average of five tests, each with three replicates, in Florida citrus field trials (FT) under mid-summer conditions when 1.3 cm rain occurred in about 45 minutes after treatment for GG (1.7/76 cm/18) in FT, GG (1.7/76 cm/30) in FT, GG (1.7/50 cm/27) in FT, GG (1.7/50 cm/26) in FT, and GG (1.7/125 cm/30) in FT are set out in Table 8.

TABLE 8

| Herb. Composition | % Inhibition | |
|---|---|---|
| | 0 Rain | Rain |
| RU | 96 | 35 |
| Formu B | 90 | 59 |
| RU + 0.2% L-77 | 93 | 67 |
| RU + 0.5% Diol 3 | 96 | 81 |
| RU + 0.2% Diol 3 | 94 | 77 |

From the above it can be seen that the rainfastness of glyphosate is significantly greater in the two tested compositions each containing Diol 3 as a cosurfactant with the ethoxylated tallowamine in RU as compared to when ethoxylated tallowamine was used as the sole surfactant, when L-77 was used in combination with Ethoquad C/12W, and when L-77 and the ethoxylated tallowamine in RU were used as cosurfactants.

EXAMPLE 6

In this example using tank mixes a comparison was made of the rainfastness when RU was used at a rate of 1.7 kg a.e./ha active, when RU was used at the same rate with Silwet L-77 and when RU was used at the same rate with Diol 3 present in two different concentrations. In this example the treatments were conducted in Southeast Asia. The formulations were applied with a mistblower applicator at approximately 35 l/ha spray volume to Pueraria sp., a two year old cover crop and to *Paspalum conjugatum*, which ranged in height between 46-90 cms at the time of treatments. The plants were growing under hot, humid tropical conditions. A tropical rain occurred one hour after treatment. % Inhibition was determined 60 days after treatments. The data for the treatment of Pueraria sp. are set out in Table 9; and the data for the treatment of *Paspalum conjugatum* are set out in Table 10.

TABLE 9

| Herb. Composition | % Inhibition | |
|---|---|---|
| | 0 Rain | Rain |
| RU | 100 | 30 |
| RU + 0.1% Diol 3 | 100 | 100 |
| RU + 0.2% Diol 3 | 100 | 100 |
| RU + 0.2% L-77 | 100 | 100 |

TABLE 10

| Herb. Composition | % Inhibition | |
|---|---|---|
| | 0 Rain | Rain |
| RU | 100 | 30 |
| RU + 0.1% Diol 3 | 100 | 100 |
| RU + 0.2% Diol 3 | 100 | 100 |
| RU + 0.2% L-77 | 100 | 100 |

From the above it can be seen that both Silwet L-77 and Diol 3 provided complete glyphosate rainfastness when added to RU under the conditions of the tests.

EXAMPLE 7

In this example using tank mixes a comparison was made of the rainfastness when RU was used at a rate of 0.42 kg a.e./ha, when RU was used at the same rate with Diol 3 and when RU was used at the same rate with Diol 4.

The average results of five tests, each with three replicates, for DB (0.42/23/28) in GC, IM (0.42/23/28) in GC, RQC (0.42/54/27) in GC, WT(0.13./23/27) in GC, and BG (0.56/20/29) in GH are set out in Table 11.

TABLE 11

| Herb. Composition | % Inhibition | |
|---|---|---|
| | 0 Rain | Rain |
| RU | 72 | 30 |
| RU + 0.25% Diol 3 | 91 | 63 |
| RU + 0.25% Diol 4 | 85 | 41 |

The average results of three replicates for GG (1.7/46/27) in GH are set out in Table 12 where three additional acetylenic diols were used with RU.

TABLE 12

| Herb. Composition | % Inhibition | |
|---|---|---|
| | 0 Rain | Rain |
| RU | 100 | 18 |
| RU + 0.5% Diol 1 | 98 | 47 |
| RU + 0.5% Diol 2 | 100 | 37 |
| RU + 0.5% Diol 3 | 100 | 40 |

From the above data it can be seen that when used as a cosurfactant, acetylenic diols having various degrees of ethoxylation significantly enhanced the rainfastness of the RU composition.

EXAMPLE 8

In this example using tank mixes a comparison was made of the enhancement of glyphosate weed control when RU was used at various acid equivalent rates, when RU was used at the same active rates with additional ethoxylated (15EO) tallowamine, and when RU was used at the same active rates with Diol 3.

The average results of four tests, each with three replicates, for WT (0.14/23/27) in GC, RQG (0.43/54/27) in GC, DB (0.28/23/28) in GC, and IM (0.28/23/28) in GC are set out in Table 13.

TABLE 13

| Herb. Composition | & Inhibition |
|---|---|
| RU | 59 |
| RU + 0.125% tallowamine | 71 |
| RU + 0.25% tallowamine | 76 |
| RU + 0.125% Diol 3 | 88 |
| RU + 0.25% Diol 3 | 86 |

From the above it can be seen that Diol 3 enhances the herbicidal activity of RU to a significantly greater extent than a similar amount of added ethoxylated tallowamine.

EXAMPLE 9

In this example using tank mixes a comparison was made of the enhancement of glyphosate weed control when RU was used alone and when RU was used with various diols as a cosurfactant.

The average results of four tests, each with three replicates, for DB (0.28/2827) in GC, IM (0.27/28/27) in GC, AB (0.28/30/27) in GC, and RF (0.56/3027) in GC are set out in Table 14.

TABLE 14

| Herb. Composition | % Inhibition |
|---|---|
| RU | 60 |
| RU + 0.0625% Diol 5 | 74 |
| RU + 0.125% Diol 5 | 65 |
| RU + 0.0625% Diol 1 | 73 |
| RU + 0.125% Diol 1 | 64 |
| RU + 0.0625% Diol 2 | 78 |
| RU + 0.125% Diol 2 | 74 |
| RU + 0.0625% Diol 3 | 79 |
| RU + 0.125% Diol 3 | 83 |
| RU + 0.0625% Diol 4 | 61 |
| RU + 0.125% Diol 4 | 68 |

From the above it can be seen that Diol 1, Diol 2, Diol 3, Diol 4, and Diol 5 all enhance the herbicidal activity of RU under the test conditions.

EXAMPLE 10

In this example using tank mixes a comparison was made of glyphosate weed control when IPA glyphosate was used with Ethoquad C/12W surfactant alone and when IPA glyphosate was used with Ethoquad C/12W (35% a.i.) and various acetylenic diols at three different rates.

The average results of two tests, each with three replicates, for BF (0.43/18/21) in GH and VL (0.43/18/21) in GH are set out in Table 15.

TABLE 15

| Herb. Composition | % BG Control | % VL Control |
|---|---|---|
| IPA gly + 0.5% Ethoquad | 73 | 13 |
| IPA gly + 0.5% Ethoquad + 0.0125% Diol 2 | 81 | 67 |

TABLE 15-continued

| Herb. Composition | % BG Control | % VL Control |
|---|---|---|
| IPA gly + 0.5% Ethoquad + 0.025% Diol 2 | 88 | 79 |
| IPA gly + 0.5% Ethoquad + 0.05% Diol 2 | 63 | 81 |
| IPA gly + 0.5% Ethoquad + 0.0125% Diol 6 | 94 | 95 |
| IPA gly + 0.5% Ethoquad + 0.025% Diol 6 | 96 | 93 |
| IPA gly + 0.5% Ethoquad + 0.5% Diol 6 | 98 | 86 |
| IPA gly + 0.5% Ethoquad + 0.125% Diol 3 | 89 | 76 |
| IPA gly + 0.5% Ethoquad + 0.25% Diol 3 | 93 | 83 |
| IPA gly + 0.5% Ethoquad + 0.5% Diol 3 | 88 | 88 |
| IPA gly + 0.5% Ethoquad + 0.0125% Diol 7 | 91 | 57 |
| IPA gly + 0.5% Ethoquad + 0.025% Diol 7 | 97 | 85 |
| IPA gly + 0.5% Ethoquad + 0.5% Diol 7 | 99 | 87 |
| IPA gly + 0.5% Ethoquad + 0.125% Diol 8 | 91 | 43 |
| IPA gly + 0.5% Ethoquad + 0.25% Diol 8 | 94 | 78 |
| IPA gly + 0.5% Ethoquad + 0.5% Diol 8 | 98 | 84 |
| IPA gly + 0.5% Ethoquad + 0.125% Diol 9 | 86 | 43 |
| IPA gly + 0.5% Ethoquad + 0.25% Diol 9 | 89 | 40 |
| IPA gly + 0.5% Ethoquad + 0.5% Diol 9 | 98 | 62 |
| IPA gly + 0.5% Ethoquad + 0.125% Diol 4 | 82 | 43 |
| IPA gly + 0.5% Ethoquad + 0.25% Diol 4 | 91 | 57 |
| IPA gly + 0.5% Ethoquad + 0.5% Diol 4 | 96 | 84 |

From the above it can be seen that different acetylenic diols when used as a cosurfactant with Ethoquad C/12W provide better glyphosate weed control than when Ethoquad C/12W is used alone.

EXAMPLE 11

In this example using various formulations a comparison was made of the enhancement of glyphosate weed control where Diol 3 was used with a variety of cosurfactants in field trials. The treatments were applied in January in southern Alabama at a spray volume of 89.7 l/ha. The average results of ten tests, each with three replicates for AB (0.28/6 cm/32) in FT, AB (0.56/6 cm/32) in FT, RYE (0.28/25 cm/32) in FT, RYE (0.56/25 cm/32) in FT, AB (0.28/25 cm/32) in FT, DB(0.56/25 cm/32) in FT, RF (0.28/25 cm/32) in FT, RF (0.56/25 cm/32) in FT, and MAL (0.28/6 cm/32) in FT, MAL (0.56/6 cm/32) in FT are set out in Table 16.

Ethomeen T/25 used in these field trials has the structural formula

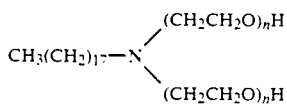

m + n = 15

Ethoquad 18/25 is the methyl 15-EO octadecyl ammonium chloride having the structural formula

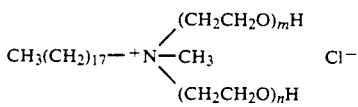

m + n = 15

Emcol CC-9 is a propoxylated quaternary amine having the structural formula

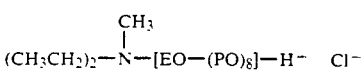

EO = ethylene oxide
PO = propylene oxide

APG 325 is an alkyl polyglycoside having the formula

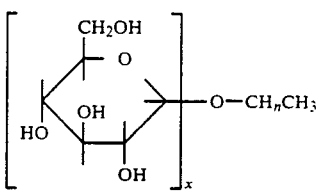

n = 9–12; x is 1.6 on average

TABLE 16

| Composition | % Inhibition |
|---|---|
| RU (0.28 a.e.) | 74 |
| RU (0.56 a.e.) | 87 |
| Formu D (0.28 a.e.) | 75 |
| Formu D (0.56 a.e.) | 90 |
| Formu E (0.28 a.e.) | 74 |
| Formu E (0.56 a.e.) | 87 |
| Formu F (0.28 a.e.) | 81 |
| Formu F (0.56 a.e.) | 89 |
| Formu G (0.28 a.e.) | 66 |
| Formu G (0.56 a.e.) | 85 |
| Formu H (0.28 a.e.) | 72 |
| Formu H (0.56 a.e.) | 90 |
| Formu I (0.28 a.e.) | 73 |
| Formu I (0.56 a.e.) | 91 |
| Formu J (0.28 a.e.) | 79 |
| Formu J (0.56 a.e.) | 94 |
| Formu K (0.28 a.e.) | 81 |
| Formu K (0.56 a.e.) | 92 |
| Formu L (0.28 a.e.) | 80 |
| Formu L (0.28 a.e.) | 91 |

As can be seen from the above, the present invention provides a stable homogeneous herbicidal composition comprising one or more salts of glyphosate, the IPA salt being the most preferred, and an acetylenic diol surfactant or an alkoxylated acetylenic diol surfactant. In dry formulations, such as water soluble granules, wettable powders, tablets, etc., a cosurfactant may or may not be an ingredient of the composition. If the composition is formulated as an aqueous concentrate, water will be a component and it is preferred that a cosurfactant of the type disclosed herein be also a component of the composition.

Furthermore, the present invention provides new and useful herbicidal compositions wherein enhancement of the rainfastness of glyphosate-based formulations by the inclusion in the compositions an acetylenic diol surfactant, optionally together with a cosurfactant of the type disclosed herein, is obtained. The rainfastening property of the compositions of the present invention represents an improvement over the rainfastening properties of organosiloxane surfactants as exemplified by Silwet L-77. Thus, the glyphosatecontaining compositions of the present invention are more efficacious as compared to comparable organosiloxane surfactants containing glyphosate herbicides in terms of rainfastness enhancement at lower concentrations in the spray solution. Less or no antagonism in the absence of rain is observed and no need exists for the addition of a humectant. The acetylenic diol surfactants used in formulating the compositions of the present invention are chemically stable therein while the organosiloxanes tend to degrade over time in similar compositions.

Also, the present invention provides in many cases efficacy enhancement of glyphosate based formulations even in the absence of rain owing to the presence therein of an efficacy-enhancing amount of an acetylenic diol surfactant. As compared with the most widely used surfactant for enhancing glyphosate efficacy, namely ethoxylated (15EO) tallowamine, the use of acetylenic diol results in a significantly improved enhancement of the herbicidal activity. In other words, the enhancement is appreciably greater with the selected acetylenic diol surfactant than the best known glyphosate activity enhancing surfactant when used at equal concentration in spray solutions.

It is important to note that the present invention provides a new and useful composition comprising glyphosate and/or one or more water soluble salts of glyphosate, an alkoxylated acetylenic diol surfactant, and a second cosurfactant selected from alkyl glycosides or alkyl polyglycosides, ethoxylated tertiary amines, ethoxylated quaternary amines, nonethoxylated and propoxylated quaternary amines, nonalkoxylated quaternary amines, and ethoxylated amine oxides. The compositions show herbicidal efficacy at least equal to or better than IPA glyphosate formulated in an aqueous solution with ethoxylated (15EO) tallowamine.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A method of controlling vegetation by the use of a glyphosate-containing herbicidal composition applied to foliage of plants comprising the steps of:
   1. intimately mixing the following ingredients to form an aqueous solution
      (a) a herbicidally effective amount of glyphosate and/or glyphosate salt;
      (b) about 0.01 part to about 1 part of an acetylenic diol surfactant having the following structural formula per part of glyphosate acid equivalent:

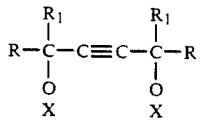

wherein X is hydrogen of $(R_2O)_n$—H where $R_2$ is ethylene and n is the average number of repeating ethylene oxide units with n being a number of 1 to about 100, R is hydrogen or lower alkyl group containing 1 to about 8 carbon atoms and $R_1$ is methyl, ethyl, cyclopropyl, or phenyl;
      (c) about 0.01 part to about 1 part of a propoxylated quaternary amine surfactant having the following formula per part of glyphosate acid equivalent:

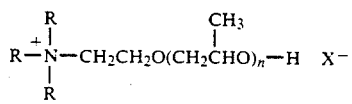

wherein each R in the amine is independently methyl, ethyl or hydroxy $C_1$–$C_3$ alkyl and n has an average value of about 6–10 and X is a suitable anion; and
      (d) water;
   2. applying the resulting solution of step 1 to foliage of plants;
   whereby the solution has enhanced resistance from being removed form the plants by a subsequently applied gentle spray of water.

2. The method of claim 1 wherein the acetylenic diol is oxyethylated or nonoxyethylated 2,5,8,11-tetramethyl-6-dodecyne-5,8-diol or oxyethylated or nonoxyethylated 2,4,7,9-tetramethyl-5-decyne-4,7-diol.

3. The method of claim 2 wherein the average number of ethylene oxide units is about 1.3.

4. The method of claim 2 wherein the average number of ethylene oxide units is about 3.5.

5. The method of claim 2 wherein the average number of ethylene oxide units is about 10.

6. The method of claim 2 wherein the average number of ethylene oxide units is about 30.

7. A glyphosate-containing herbicidal composition in aqueous solution comprising
   (a) a herbicidally effective amount of glyphosate and/or glyphosate salt;
   (b) about 0.01 part to about 1 part per part of of an acetylenic diol surfactant having the following structural formula per part of glyphosate equivalent:

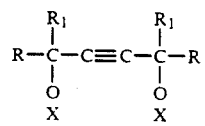

wherein X is hydrogen or $(R_2O)_n$—H where $R_2$ is ethylene and n is the average number of repeating ethylene oxide units with n being a number of 1 to about 100, R is hydrogen or lower alkyl group containing 1 to about 8 carbon atoms and $R_1$ is methyl, ethyl, cyclopropyl, or phenyl;
   (c) about 0.01 part to about 1 part of a propoxylated quaternary amine surfactant having the following formula per part of glyphosate acid equivalent:

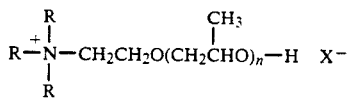

wherein each R in the amine is independently methyl, ethyl or hydroxy $C_1$–$C_3$ alkyl and n has an average value of about 6–10 and X is a suitable anion and
   (d) water;
   whereby when the composition is applied to foliage of plants to be controlled, the solution has enhanced resistance from being removed from the plants by a gentle spray of water.

8. The composition of claim 7 wherein the acetylenic diol is oxyethylated or nonoxyethylated 2,5,8,11-tetramethyl-6-dodecyne-5,8-diol or oxyethylated or nonoxyethylated 2,4,7,9-tetramethyl-5-decyne-4,7-diol.

9. The composition of claim 8 wherein the average number of ethylene oxide units is about 1.3.

10. The composition of claim 8 wherein the average number of ethylene oxide units is about 3.5.

11. The composition of claim 8 wherein the average number of ethylene oxide units is about 10.

12. The composition of claim 8 wherein the average number of ethylene oxide units is about 30.

* * * * *